US008759021B2

(12) United States Patent
Park et al.

(10) Patent No.: US 8,759,021 B2
(45) Date of Patent: Jun. 24, 2014

(54) MICROORGANISM FOR QUANTIFYING HOMOCYSTEINE, AND USE THEREOF

(75) Inventors: Hyun Gyu Park, Daejeon (KR); Min-Ah Woo, Daejeon (KR); Moon Il Kim, Daejeon (KR); Sang-Joon Hwang, Seoul (KR); Dae-Yeon Cho, Gyeonggi-do (KR)

(73) Assignee: Labgenomics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 13/698,924

(22) PCT Filed: May 20, 2010

(86) PCT No.: PCT/KR2010/003184
§ 371 (c)(1),
(2), (4) Date: Nov. 19, 2012

(87) PCT Pub. No.: WO2011/145764
PCT Pub. Date: Nov. 24, 2011

(65) Prior Publication Data
US 2013/0095497 A1 Apr. 18, 2013

(51) Int. Cl.
*C12Q 1/02* (2006.01)
*C12Q 1/04* (2006.01)
*C12P 1/00* (2006.01)
*C12N 1/00* (2006.01)
*C12N 1/12* (2006.01)
*C12N 1/20* (2006.01)

(52) U.S. Cl.
USPC ............... 435/29; 435/34; 435/41; 435/243; 435/252.1; 435/252.8

(58) Field of Classification Search
None
See application file for complete search history.

(56) References Cited

U.S. PATENT DOCUMENTS 6,066,467 A 5/2000 Xu et al.
2005/0019937 A1 1/2005 Shiue et al.

FOREIGN PATENT DOCUMENTS

WO 2008/133464 A1 * 11/2008 ............... C12Q 1/02

OTHER PUBLICATIONS

Dev et al., "Regulation of Synthesis of Serine Hydroxymethyltransferase in Chemostat Cultures of *Escherichia coli*" 259(13) The Journal of Biological Chemistry 8394-8401 (1984).*
Mulligan et al., "An assay for betaine-homocysteine methyltransferase activity based on the microbiological detection of methionine" 9 Journal of Nutritional Biochemistry 351-354 (1998).*
Tani et al., "Chip-Based Bioassay Using Bacterial Sensor Strains Immobilized in Three-Dimensional Microfluidic Network" 76 Analytical Biochemistry 6693-6697 (2004).*
Simon et al., "Direct Homocysteine Biosynthesis from O-Succinylhomoserine in *Escherichia coli*: an Alternate Pathway That Bypasses Cystathionine" 153(1) Journal of Bacteriology 558-561 (1983).*
Dev et al., "Role of Methionine in the Regulation of the Synthesis of Serine Hydroxymethyltransferase in *Excherichia coli*" 259(13) The Journal of Biological Chemistry 8402-8406 (1984).*
Bialecka et al. (May-Jun. 2009) "Genetic and Environmental Factors for Hyperhomocysteinaemia and Its Clinical Implications in Parkinson's Disease," Neurologia i Neurochirurgia Polska 43(3):272-285.
Blommel et al. (2007) "Enhanced Bacterial Protein Expression During Auto-Induction Obtained by Alteration of Lac Repressor Dosage and Medium Composition," Biotechnol Prog 23:585-598.
Datsenko et al. (2000) "One-Step Inactivation of Chromosomal Genes in *Escherichia coli* K-12 Using PCR Products," PNAS 97(12):6640-6645.
Dietzen et al. (2008) "Rapid Comprehensive Amino Acid Analysis by Liquid Chromatography/Tandem Mass Spectrometry: Comparison to Cation Exchange with Post-Column Ninhydrin Detection," Rapid Commun Mass Spectrom 22:3481-3488.
Le Boucher et al. (1997) "Amino Acid Determination in Biological Fluids by Automated Ion-Exchange Chromatography: Performance of Hitachi L-8500A," Clinical Chemistry 43(8):1421-1428.
Lyi et al. (2007) "Biochemical and Molecular Characterization of the Homocysteine S-Methyltransferase from Broccoli (*Brassica oleracea var. italica*)," Phytochemistry 68:1112-1119.
Molloy et al. (Apr. 2009) "The Search for Genetic Polymorphisms in the Homocysteine/Folate Pathway That Contribute to the Etiology of Human Neural Tube Defects," Birth Defects Research (Part A) 85:285-294.
Nilsson et al. (2008) "Plasma Homocysteine and Vascular Disease in Elderly Patients with Mental Illness," Clin Chem Lab Med 46(11):1556-1561.
Papatheodorou et al. (2007) "Vascular Oxidant Stress and Inflammation in Hyperhomocysteinemia," Antioxidants & Redox Signaling 9(11):1941-1958.
Refsum et al. (2004) "Facts and Recommendations about Total Homocysteine Determinations: An Expert Opinion," Clinical Chemistry 50(1):3-32, published electronically May 13, 2008.
Reznikoff et al. (2004) "Tn5 as a Molecular Genetics Tool," Methods in Molecular Biology 260:83-96.
Seshadri et al. (2002) "Plasma Homocysteine as a Risk Factor for Dementia and Alzheimer's Disease," N Engl J Med 346(7):476-483.
Van Dam et al. (2009) "Hyperhomocysteinemia and Alzheimer's Disease: A Systematic Review," Archives of Gerontology and Geriatrics 48:425-430.
Van Meurs et al. (2004) "Homocysteine Levels and the Risk of Osteoporotic Fracture," N Engl J Med 350(20):2033-2041.
Weiss N. (2005) "Mechanisms of Increased Vascular Oxidant Stress in Hyperhomocysteinemia and Its Impact on Endothelial Function," Current Drug Metabolism 6:27-36.
Wheeler S. (2008) "Assessment and Interpretation of Micronutrient Status During Pregnancy," Symposium on 'Translation of research in nutrition II: the bed', Proceedings of the Nutrition Society 67:437-450.
Yoshida et al. (2003) "Homocysteine Biosynthesis Pathways of *Streptococcus anginosus*," FEMS Microbiology Letters 221:277-284.

(Continued)

*Primary Examiner* — Jennifer Dunston
*Assistant Examiner* — Nancy J. Leith
(74) *Attorney, Agent, or Firm* — Lathrop & Gage LLP

(57) ABSTRACT

Provided are a microorganism for use in quantification of homocysteine and methionine and a method of quantifying homocysteine and methionine in a sample by using the microorganism.

5 Claims, 6 Drawing Sheets

(56) References Cited

OTHER PUBLICATIONS

Fraser et al. (2006), "Global effects of homocysteine on transcription in *Escherichia coli*: induction of the gene for the major cold-shock protein, CspA," Microbiology (2006), 152,2221-2231.

Tuite et al. (2005), "Homocysteine Toxicity in *Escherichia coli* Is Caused by a Perturbation of Branched-Chain Amino Acid Biosynthesis" Journal of Bacteriology, vol. 187, No. 13, p. 4362-4371.

* cited by examiner

MICROORGANISM FOR QUANTIFYING HOMOCYSTEINE, AND USE THEREOF

CROSS-REFERENCE TO RELATED APPLICATIONS

This application is a U.S. National Stage Application under 35 U.S.C. §371 of International Application No. PCT/KR2010/003184, filed May 20, 2010, which is hereby incorporated by reference in its entirety.

TECHNICAL FIELD

The present invention has been obtained from a study performed under the Small and Medium Business Technology Innovation Development Project sponsored by Small and Medium Business Administration.

[Project No.: S1060417, Project name: Development of microorganism sensor-based biochip for neonatal screening test]

The present invention relates to microorganism for use in quantitative analysis of homocysteine and methionine and method for quantitative analysis of homocysteine and methionine by using the microorganism.

BACKGROUND ART

Total concentration of homocysteine (Hcy) in body fluid, such as plasma or serum, has been known as an important marker for several specific diseases. Since a critical role of Hcy in human body was introduced in the late 1960s, many clinical studies have demonstrated that Hcy is a prognostic maker of cardiovascular disease and pathogenesis of atherosclerosis. Although the pathogenesis mechanism of these diseases by Hcy has not been fully understood, efforts for clearly establishing the role of Hcy in such diseases are ongoing in clinical and basic medical fields. Regarding cardiovascular disease, it is reported that elevated Hcy level triggers increased oxidant stress in the vasculature (Weiss, N. *Curr-Drug Metab* 2005, 6, 27-36; Papatheodorou, L.; Weiss, N. *Antioxid Redox Signal* 2007, 9, 1941-1958). The elevated Hcy level known as hyperhomocysteinemia is also associated with Alzheimer's disease (Seshadri, S.; Beiser, A.; Selhub, J.; Jacques, P. F.; Rosenberg, I. H.; D'Agostino, R. B.; Wilson, P. W.; Wolf, P. A. *N Engl J Med* 2002, 346, 476-483; Nilsson, K.; Gustafson, L.; Hultberg, B. *Clin Chem Lab Med* 2008, 46, 1556-1561; Van Dam, F.; Van Gool, W. A. *Arch Gerontol Geriatr* 2009, 48, 425-430), Parkinson's disease (Bialecka, M.; Robowski, P.; Honczarenko, K.; Roszmann, A.; Slawek, J. *Neurol Neurochir Pol* 2009, 43, 272-285), neural tube defects (Molloy, A. M.; Brody, L. C.; Mills, J. L.; Scott, J. M.; Kirke, P. N. *Birth Defects Res A Clin Mol Teratol* 2009, 85, 285-294), pregnancy complications (Wheeler, S. *Proc Nutr Soc* 2008, 67, 437-450), and osteoporosis (van Meurs, J. B.; Dhonukshe-Rutten, R. A.; Pluijm, S. M.; van der Klift, M.; de Jonge, R.; Lindemans, J.; de Groot, L. C.; Hofman, A.; Witteman, J. C.; vanLeeuwen, J. P.; Breteler, M. M.; Lips, P.; Pols, H. A.; Uitterlinden, A. G. *N Engl J Med* 2004, 350, 2033-2041). In fact, the balance between Hcy production and utilization can be disturbed by the clinical states characterized by genetic disorders. Thus, a simple and accurate quantitative analysis method for Hcy is needed to diagnose the above-mentioned diseases and newborn defects in metabolism.

Nowadays, some methods for quantifying Hcy involve traditional analytical techniques such as high-performance liquid chromatography (HPLC), gas chromatography-mass spectrometry (GC-MS), and immunoassay. These methods have been widely used for Hcy quantification in the clinical monitoring of biological fluids, however, they have the disadvantages of complication and inefficiency of labeling, poor stability, and relatively low intensities of dyes. In addition, they require expensive and highly specialized analysis equipment and trained operators, and thus they are often costly, and time-consuming to perform. Accordingly, there is a need to develop a simple, cheap, and highly accurate and sensitive Hcy quantification method in order to effectively detect and quantify Hcy, a disease marker.

For the development, we performed studies on self-luminescent/fluorescent Hcy/methionine auxotroph microorganism having optimal growth characteristics under assay environments, and Hcy/methionine quantitative analysis methods based on the microorganism, and finally developed a microorganism that grows in proportion to the amount of Hcy/methionine in a sample and exhibits a luminescent or fluorescent signal by the proportional amount of the growth.

DETAILED DESCRIPTION OF THE INVENTION

Technical Problem

The present invention provides a microorganism for use in cell-based quantitative analysis of homocysteine and methionine.

The present invention also provides a method for cell-based quantitative analysis of homocysteine and methionine by using the microorganism.

Technical Solution

One aspect of the present invention provides a microorganism which is homocysteine and methionine auxotroph and expresses a fluorescent protein or luciferase.

According to an embodiment of the present invention, the microorganism which is homocysteine and methionine auxotroph contains a gene encoding luciferase or fluorescent protein, and expression of the gene is proportional to the growth of microorganism.

According to an embodiment of the present invention, the microorganism may be *Escherichia coli* MetB$^-$ deposited under the Accession No. KCCM11069P.

The *Escherichia coli* MetB$^-$ grows in minimal media in proportion to the concentration of homocysteine and methionine, and expresses luciferase in proportion to the growth. The luminescent intensity of luciferase according to the growth of *Escherichia coli* MetB$^-$ has a strong linear relationship with the concentrations of homocysteine and methionine. In addition, since *Escherichia coli* MetB$^-$ has high growth rate, quantitative analysis may be performed within a short period of time, for example, 3 to 4 hours of culturing. Accordingly, *Escherichia coli* MetB$^-$ may be effectively used to quantify homocysteine and methionine in a sample.

Another aspect of the present invention provides *Escherichia coli* Met5$^-$ deposited under the Accession No. KCCM11070P which is methionine auxotroph and expresses luciferase.

The *Escherichia coli* Met5$^-$ grows in a minimal media in proportion to the concentration of methionine and expresses luciferase in proportion to the growth. The luminescent intensity of luciferase according to the growth of *Escherichia coli* Met5$^-$ has a strong linear relationship with the concentration of methionine. In addition, since *Escherichia coli* MetB$^-$ has high growth rate, quantitative analysis may be performed within a short period of time, for example, 3 to 4 hours of culturing. Accordingly, *Escherichia coli* Met5⁻ may be effectively used to quantify homocysteine and methionine in a sample.

Another aspect of the present invention provides a composition for quantifying homocysteine, the composition including *Escherichia coli* MetB⁻ and *Escherichia coli* Met5⁻.

According to an embodiment of the present invention, the composition may further include a minimal media for culturing *Escherichia coli*, a transcription inducer for inducing expression of luciferase, and a substrate for the luciferase.

According to an embodiment of the present invention, the transcription inducer may be isopropyl-1-thio-β-D-galactopyranoside (IPTG), and the substrate for the luciferase may be luciferin.

According to an embodiment of the present invention, the composition for quantifying homocysteine, including *Escherichia coli* MetB⁻ and *Escherichia coli* Met5⁻, may be used to quantify homocysteine in a sample by culturing each of *Escherichia coli* MetB⁻ and *Escherichia coli* Met5⁻ in a sample, adding a substrate for luciferase, measuring the amount of expressed luciferase, calculating the content of homocysteine and methionine and the content of methionine from the measured results, and subtracting the methionine content from the content of homocysteine and methionine. That is, from standard curves showing relationship between the growth of *Escherichia coli* MetB⁻ and *Escherichia coli* Met5⁻ and the concentrations of homocysteine/methionine and methionine, the content of homocysteine and methionine, and the content of methionine are obtained, and then, the content of methionine is subtracted from the content of homocysteine and methionine to obtain the content of homocysteine in a sample.

Another aspect of the present invention provides a biochip for quantifying homocysteine, the biochip including *Escherichia coli* MetB⁻ and *Escherichia coli* Met5⁻ immobilized on a planar substrate.

According to an embodiment of the present invention, the planar substrate may be formed of material selected from plastic, glass, silicon, hydrogel, ceramic, metal, and porous film.

According to an embodiment of the present invention, the biochip may be prepared on a micro-well plate.

According to an embodiment of the present invention, the immobilization may be achieved by using immobilization material selected from agar, agarose, sodium alginate, sol-gel, chitosan, collagen, carrageenan, polyvinyl alcohol, polyurethane, polyethylene glycol, and polyacrylamide.

According to an embodiment of the present invention, the immobilized *Escherichia coli* may be immobilized as a suspension in a minimal media for culturing, the minimal media including a transcription inducer that induces expression of luciferase.

According to an embodiment of the present invention, the immobilization may be achieved by aliquoting a mixture of each of *Escherichia coli* MetB⁻ and *Escherichia coli* Met5⁻ cultures and a sterilized agar solution in each well of a micro-well plate, followed by solidification.

According to an embodiment of the present invention, a sample and an inducer for the expression of luciferase are added to each well of the microwell plate on which each of *Escherichia coli* MetB⁻ and *Escherichia coli* Met5⁻ are immobilized, and then, after incubation at the temperature of 37° C. for 4 hours, luminescent intensities of the *Escherichia coli* MetB⁻ and *Escherichia coli* Met5⁻ are measured and from the result, the content of homocysteine content in the sample is obtained. That is, from standard curves showing relationships between the growth of *Escherichia coli* MetB⁻ and *Escherichia coli* Met5⁻ and the concentration of homocysteine/methionine and methionine, the content of homocysteine and methionine, and the content of methionine are calculated, and then, the content of methionine is subtracted from the content of homocysteine and methionine to obtain the content of homocysteine content in the sample.

Another aspect of the present invention provides a method of qualifying homocysteine in a sample by using an auxotrophic mutant of *Escherichia coli*. The method includes measuring the content of homocysteine and methionine in the sample by culturing homocysteine and methionine auxotrophic mutants of *Escherichia coli* in the sample, measuring the content of methionine in the sample by culturing methionine auxotrophic mutants of *Escherichia coli* in the sample, and determining the content of homocysteine by subtracting the content of methionine from the content of homocysteine and methionine in the sample.

According to an embodiment of the present invention, the *Escherichia coli* mutants may contain a gene that encodes a marker expressing fluorescence or luminescence in proportion to its growth.

According to an embodiment of the present invention, the *Escherichia coli* mutants may contain a gene that encodes a fluorescent protein, such as a green fluorescent protein (GFP), and the gene may express in proportion to the growth of the *Escherichia coli* mutant.

According to an embodiment of the present invention, the *Escherichia coli* mutants contain a gene encoding luciferase, and the gene may express in proportion to the growth of the *Escherichia coli* mutants.

According to an embodiment of the present invention, the *Escherichia coli* mutant having homocysteine and methionine auxotrophic phenotypes may be *Escherichia coli* MetB⁻, and the *Escherichia coli* mutant having methionine auxotrophic phenotype may be *Escherichia coli* Met5⁻.

According to an embodiment of the present invention, the sample may be an assay sample containing homocysteine or methionine. For example, the sample may be body fluid such as blood, urine and serum, but is not limited thereto.

According to an embodiment of the present invention, the content of homocysteine and methionine may be measured from an amount of expressed fluorescent protein or luciferase. *Escherichia coli* MetB⁻ is an auxotrophic mutant that requires homocysteine and methionine for its growth in a minimal media, and *Escherichia coli* Met5⁻ is an auxotrophic mutant that requires methionine for its growth in a minimal media, and *Escherichia coli* MetB⁻ and *Escherichia coli* Met5⁻ express luciferase according to their growth, and their expression levels of luciferase have a strong linear relationship with the content of homocysteine and methionine in the sample. Accordingly, from a standard curve showing a relationship between a luminescent intensity from the luciferase expressed after *Escherichia coli* MetB⁻ and *Escherichia coli* Met5⁻ are cultured, and the concentration of homocysteine and methionine, the luminescent intensity is converted into the content of homocysteine and methionine in a sample.

According to an embodiment of the present invention, the culturing of *Escherichia coli* MetB⁻ or *Escherichia coli* Met5⁻ in the sample may be performed after the sample is mixed with a transcription inducer for the expression of luciferase in *Escherichia coli* MetB⁻ or *Escherichia coli* Met5⁻. Since *Escherichia coli* MetB⁻ or *Escherichia coli* Met5⁻ is a strain that is transformed by pTAC-lux, which is a recombined vector including a gene encoding luciferase, a transcription inducer, such as isopropyl-1-thio-β-D-galactopyranoside (IPTG), needs to be added thereto to induce expression of luciferase.

According to an embodiment of the present invention, the measuring of the content of homocysteine or methionine in the sample may further include, after the culturing of the *Escherichia coli* MetB⁻ or *Escherichia coli* Met5⁻ in the sample, reacting the sample with a substrate for luciferase and measuring a luminescent intensity.

According to an embodiment of the present invention, the method may further include comparing the homocysteine content determined in the sample with a homocysteine content measured in a normal control subject.

According to an embodiment of the present invention, the method may be used to diagnose hyperhomocysteinemia.

A homocysteine concentration in normal plasma may be in a range of 5 to 15 µmol/L, and hyperhomocysteinemia is classified into four stages: (1) moderate (5 to 15 µmol/L), (2) mild (15 to 30 µmol/L), (3) intermediate (30 to 100 µmol/L), and (4) severe (>100 µmol/L). According to the method according to an embodiment of the present invention, diagnosis and progress of hyperhomocysteinemia may be monitored by measuring the homocysteine content in plasma.

According to an embodiment of the present invention, the method may be used to diagnose at least one disease selected from cardiovascular disease, neural tube defects, pregnancy complications, osteoporosis, and Alzheimer's disease.

According to an embodiment of the present invention, the homocysteine quantification method may be performed on a biochip with *Escherichia coli* mutants immobilized on a planar substrate.

Hereinafter, the present invention is described in detail with reference to examples. However, the examples are presented herein for illustrative purpose only, and the present invention is not limited thereto.

Advantageous Effects

*Escherichia coli* mutants according to the present invention and homocysteine quantitative analysis methods using the same may be used to quantify the content of homocysteine in a plurality of samples accurately and quickly, thereby enabling early diagnosis of hyperhomocysteinemia and disease related thereto.

EXAMPLE 1

Figure 1:
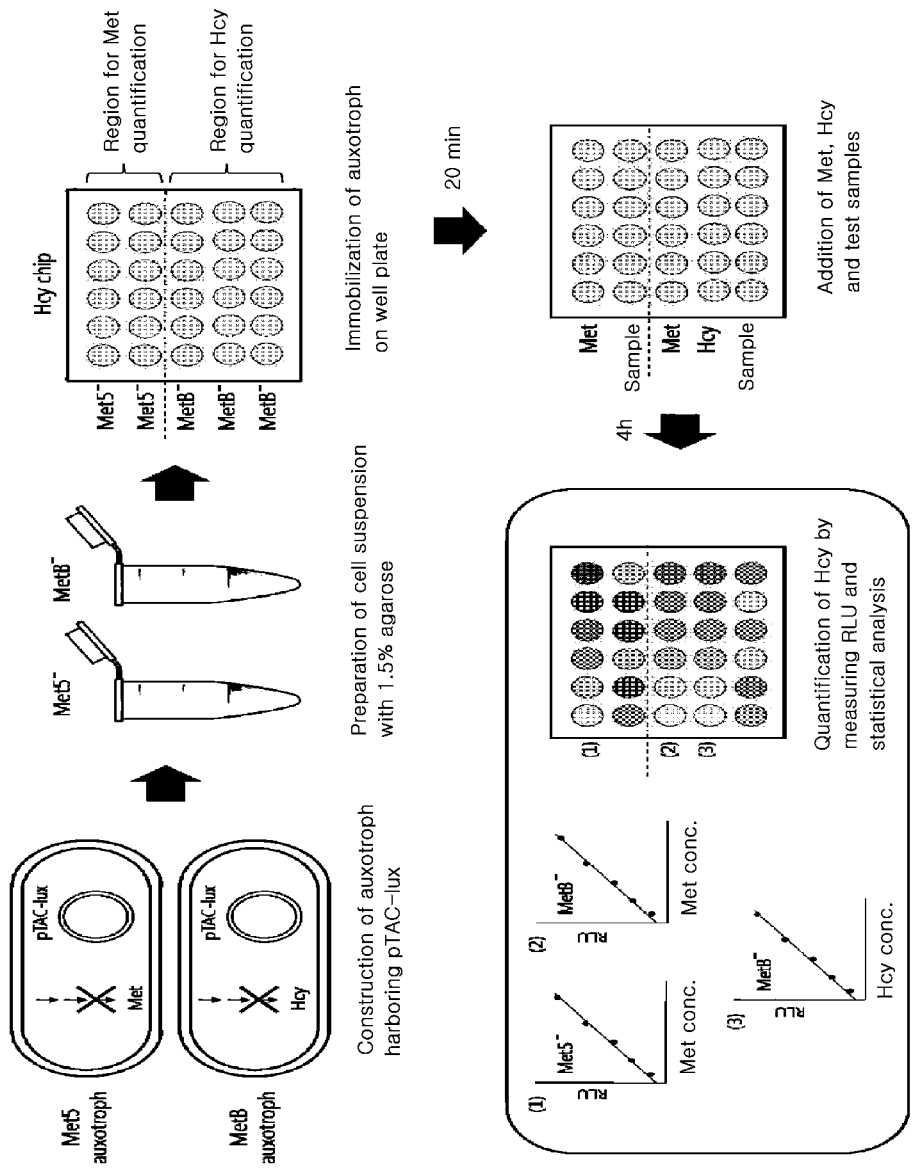
FIG. 1 schematically illustrates a method of preparing *Escherichia coli* mutants for homocysteine quantitative analysis and a method for homocysteine quantification by using the *Escherichia coli* mutants, according to embodiments of the present invention.

Preparation of Auxotrophs for Homocysteine Quantitative Analysis

An *Escherichia coli* that has homocysteine and methionine auxotrophic phenotypes and expresses luciferase and an *Escherichia coli* that has methionine auxotrophic phenotype and expresses luciferase were prepared for cell-based homocysteine quantitative analysis.

1-1. Homocysteine and Methionine Auxotrophic *Escherichia Coli*

A strain having homocysteine and methionine auxotrophic phenotypes was prepared from *Escherichia coli* (ATCC11105) by using a chromosomal gene deletion method (Datsenko, K. A.; Wanner, B. L. Proc Natl Acad Sci 2000, 97, 6640-6645). A chromosomal gene MetB of *Escherichia coli* (ATCC11105) was replaced with a linear cassette containing chloramphenicol (Cm) resistance marker that is amplified by PCR using primers set forth in SEQ ID NO: 1 and SEQ ID NO: 2, and the PCR product was transformed in *Escherichia coli* (ATCC11105). Thereafter, the *Escherichia coli* was cultured in a chloramphenicol-containing (35 µg/ml) agar plate to select MetB-gene deleted *Escherichia coli* in which the MetB gene is replaced by a Cm resistance marker. MetB is a gene that encodes cystathione γ-synthase in *Escherichia coli* and controls homocysteine biosynthesis. MetB deleted *Escherichia coli* showed a growth in proportion to concentrations of homocysteine and methionine in media. Selected MetB deleted *Escherichia coli* were cultured in Cm-containing LB media (1 g of tryptophan, 1 g of NaCl, and 0.5 g/100 ml of yeast extract) at the temperature of 37 for 2 hours, and then, they were washed three times with ice-cold water, and stored in 10% glycerol solution.

Since MetB deleted *Escherichia coli* has homocysteine and methionine auxotrophic phenotype, the auxotroph cannot be used solely to quantify homocysteine. To quantify homocysteine by using MetB deleted *Escherichia coli*, the growth due to methionine needs to be excluded from the growth of MetB deleted *Escherichia coli*. Accordingly, to prepare an *Escherichia coli* that has only methionine auxotrophic phenotype, a methionine auxotrophic mutant of *Escherichia coli* was prepared from *Escherichia coli* (ATCC11105) by transposon mutagenesis (Reznikoff, W. S., Goryshin, I. Y., Jendrisak, J. J. Tn5 as a molecular genetics tool: In vitro transposition and the coupling of in vitro technologies with in vivo transposition. *Methods Mol. Biol.* 260, 83-96 (2004)). First, 1 µl KAN-2 transposon (Epicentre, WI, USA) was introduced to *Escherichia coli* (ATCC11105) by electroporation according to standard procedures in the art. Thereafter, transposon-inserted mutant strains were selected on kanamycin (Km)-containing (50 µg/ml) agar plate. For selection of a methionine auxotroph strain from transposon-inserted mutant strains, replica plating was performed first on Km and methionine-containing M9 media (200 ml of 5× M9 salt (64 g of Na$_2$HPO$_4$.7H$_2$O, 15 g of KH$_2$PO$_4$, 2.5 g of NaCl, and 5 g of NH$_4$Cl, per 1 liter), 2 ml of 1M MgSO4, 20 ml of 20% glucose, 100 µl/liter of 1M CaCl$_2$) plate and then, only Km-containing M9 media plate. After methionine auxotroph mutant strains were selected, methionine auxotrophic phenotype was confirmed by identifying growth in M9 media with or without methionine.

1-2. Transformation with a Gene Encoding Luciferase

To quantify the growth of MetB deleted *Escherichia coli* and methionine auxotrophic *Escherichia coli* prepared in Example 1-1 according to the total concentration of homocysteine and methionine, and the concentration of methionine via expression of the recombined luminescent gene, the *Escherichia coli* was transformed with recombinant plasmid pTAC-lux containing a gene for luciferase.

First, T7lac promoter of pETDuet-1 vector (Novagen, CA, USA) was replaced by tac promoter to prepare pTAC plasmid containing IPTG-inducible promoter. Luciferase coding lux fragment was amplified using primers set forth in SEQ ID NO: 1 (NcoI-lux-F) and SEQ ID NO: 2 (EcoRI-lux-R) and pGL3-Basic vector (Promega, WI, USA) as template. The pTAC plasmid, and the amplified lux fragment were respectively cleaved by NcoI and EcoRI and then ligated to prepare recombinant plasmid pTAC-lux.

MetB deleted *Escherichia coli* and methionine auxotroph *Escherichia coli* were transformed with the recombinant plasmid pTAC-lux by electroporation using Gene Pulser system (Bio-Rad, CA, USA) to prepare homocysteine and methionine auxotrophic *Escherichia coli* that expresses luciferase and methionine auxotrophic *Escherichia coli* that expresses luciferase. The homocysteine and methionine auxotrophic *Escherichia coli* that expresses luciferase and the methionine auxotrophic *Escherichia coli* that expresses luciferase are respectively named as *Escherichia coli* MetB$^-$ and *Escherichia coli* Met5$^-$.

1-3. Specificity to Homocysteine and Methionine

MetB$^-$ and Met5$^-$ auxotrophs were cultivated in LB media containing Cm and Km, respectively, at 37° C. with shaking for 9 to 12 hours. After the cells were washed with M9 media two times, 2×10$^6$ cells were mixed with 3% low melting agarose (Sigma-Aldrich, MO, USA) at a volume ratio of 1:1. 100 µl of the cell-agarose mixture was immobilized in each of 22 wells of 96-well plate (Nunc, Roskilde, Denmark). After incubation at room temperature for 20 min, the cell-agarose mixture was solidified. 100 µl of M9 media containing 1 µl of 1 nM cyanocobalamin, 100 nM IPTG, and 20 µM amino acid (one selected from alanine, arginine, asparagine, aspartate, cysteine, glutamine, glycine, histidine, homocysteine, isoleucine, leucine, lysine, methionine, phenylalanine, serine, threonine, tyrosine, tryptophan, valine, and proline) was added to each of 21 wells, and the same medium excluding the amino acid was added to the residual well for use as control. After incubation at 37° C. for 4 hours, 100 µl of luciferin solution (1 mM D-luciferin in 0.1M sodium citrate (pH 5.0) buffer) was added thereto and a reaction was performed for 10 minutes. Thereafter, luminescence was measured using luminometer (Perkin Elmer, MA, USA), and scanned images thereof were obtained by using a cooled charge coupled device (CCD) camera (Fujifilm, Japan). *Escherichia coli* MetB$^-$ and *Escherichia coli* Met5$^-$ grew only in the presence of homocysteine and methionine, and methionine, respectively, and thus, specificity thereof to homocysteine and methionine and methionine were confirmed.

Figure 2:
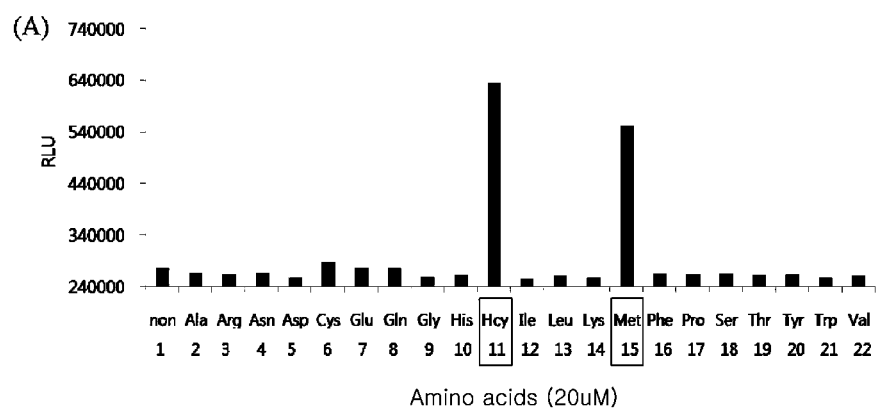
FIG. 2 shows homocysteine and methionine specific auxotrophic phenotype of *Escherichia coli* MetB⁻. (A) shows luminescent intensities measured after culturing in a minimal media containing each of 21 kinds of amino acids, and (B) shows a scanned image of well plate.
Figure 2:
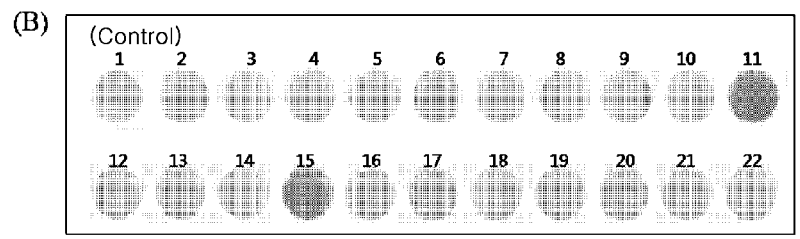

FIG. 2 shows homocysteine and methionine specific auxotrophic phenotype of *Escherichia coli* MetB$^-$.

1-4. Linearity Between Luciferase Expression and Concentrations of Homocysteine and Methionine Linearity between growth of *Escherichia coli* MetB$^-$ and *Escherichia coli* Met5$^-$ and the concentration of homocysteine and methionine was tested.

To identify a relationship between the growth of *Escherichia coli* MetB$^-$ and the concentration of homocysteine, different concentrations (0, 4, 8, 16, 32, 64, 96, and 128 mM) of homocysteine dissolved in pure water, 20 mM Met-containing water, or an amino acid cocktail solution were added to wells of a micro-well plate on which *Escherichia coli* MetB$^-$ prepared according to Example 1-3 was immobilized, and then cultured at the temperature of 37 for 4 hours. Thereafter, 100 µl of luciferin solution (1 mM D-luciferin in 0.1M sodium citrate (pH 5.0) buffer) was added to each well and after incubation for 10 minutes, luminescence was measured using luminometer (Perkin Elmer, MA, USA), and scanned images thereof were obtained by using a cooled charge coupled device (CCD) camera (Fujifilm, Japan).

Figure 3:
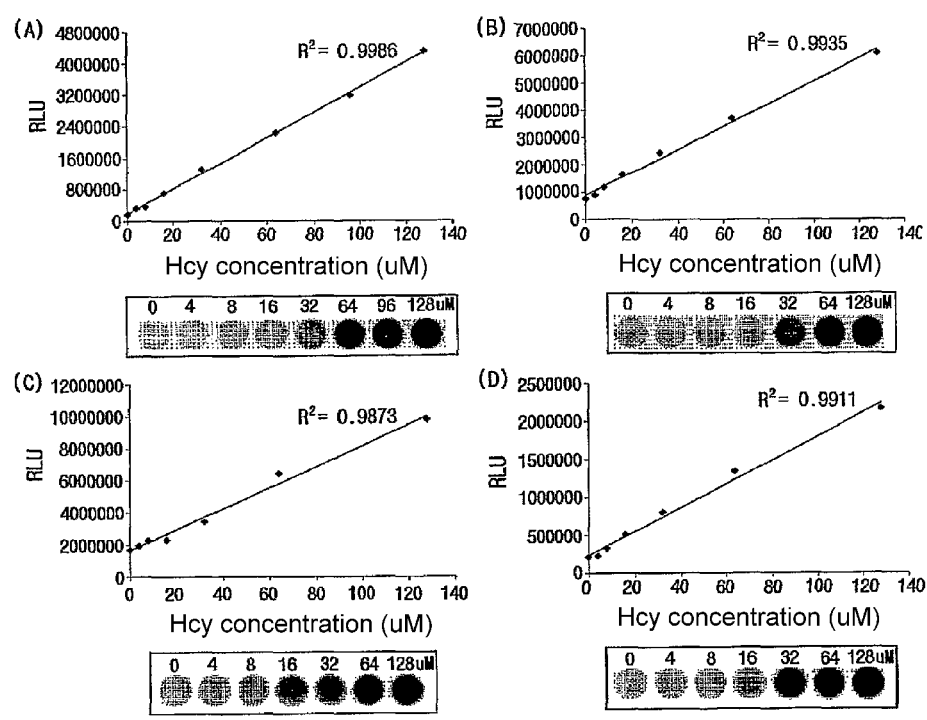
FIG. 3 shows a linearity between a luminescent intensity according to *Escherichia coli* MetB⁻ growth and a homocysteine concentration. (A) to (D) respectively show graphs of a luminescent intensity according to the *Escherichia coli* MetB⁻ growth and a concentration of homocysteine dissolved in pure water, 20 µM methionine-containing water, a 50% amino acid cocktail solution, and a 20% amino acid cocktail solution. The images below each linear graph indicate luminescent intensities according to homocysteine concentrations.

Linearity was evaluated based on the correlation between a luminescent signal according to the growth of *Escherichia coli* MetB$^-$ and the concentration of homocysteine. FIG. 3A shows linearity of $R^2$=0.9986 between the *Escherichia coli* MetB$^-$ growth and 8 different concentrations (0, 4, 8, 16, 32, 64, 96, and 128 mM) of homocysteine dissolved in pure water. FIG. 3B shows linearity between the *Escherichia coli* MetB$^-$ growth and the concentration of homocysteine dissolved in 20 mM Met-containing water. In addition, an artificial amino acid cocktail solution having a composition similar to that of blood was prepared to perform the homocysteine quantitative analysis using the *Escherichia coli* in a sample similar to a clinical sample. The amino acid cocktail solution was comprised of 300 mM alanine, 40 mM arginine, 60 mM asparagine, 3 mM aspartate, 45 mM cysteine, 500 mM glutamine, 50 mM glutamate, 220 mM glycine, 65 mM histidine, 65 mM isoleucine, 100 mM leucine, 180 mM lysine, 20 mM methionine, 50 mM phenylalanine, 100 mM serine, 120 mM threonine, 60 mM tyrosine, 20 mM tryptophan, 220 mM valine, and 200 mM proline. All amino acids were purchased from Sigma-Aldrich (MO, USA). FIGS. 3C and 3D show the linearity between luminescence according to the growth of *Escherichia coli* MetB$^-$ and concentrations of 0 to 128 mM homocysteine dissolved in 50% amino acid cocktail solution and 20% amino acid cocktail solution, respectively. These results show that homocysteine dissolved in 20% amino acid cocktail solution ($R^2$=0.9911, FIG. 3D) showed more distinctive linearity than homocysteine dissolved in 50% amino acid cocktail solution ($R^2$=0.9873, FIG. 3C). Accordingly, 20% amino acid cocktail solution or 20% plasma was determined as an optimal concentration for quantifying the concentration of homocysteine in a test sample.

Figure 4:
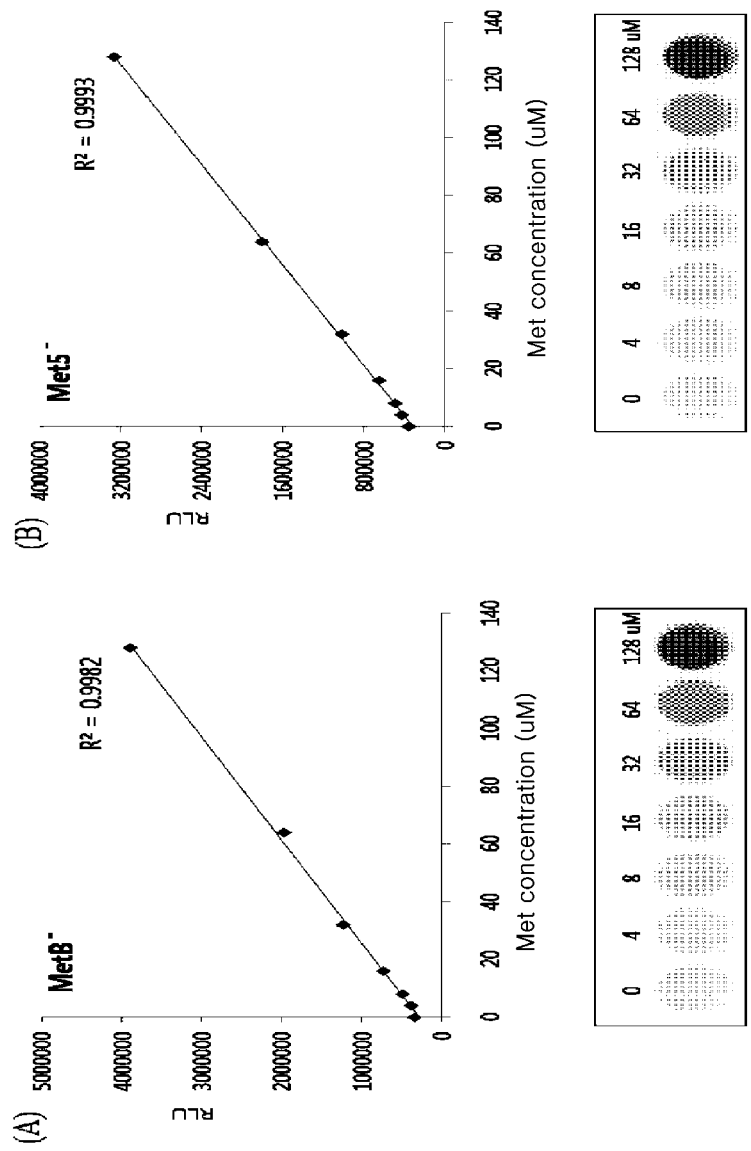
FIG. 4 shows a linearly proportional relationship between a luminescent intensity according to the growth of *Escherichia coli* MetB⁻ (A) and *Escherichia coli* Met5⁻ (B) and a methionine concentration, and luminescent intensities according to methionine concentrations.

In addition, luminescence according to the growth of *Escherichia coli* MetB$^-$ and *Escherichia coli* Met5$^-$ showed linearity with respect to the concentration of methionine dissolved in pure water. FIGS. 4A and 4B show relationships between the luminescence according to the growth of respective *Escherichia coli* MetB⁻ and *Escherichia coli* Met5⁻ and the concentration of methionine.

*Escherichia coli* Met5⁻ did not produce any luminescent signal when luminescence thereof was measured after cultured in the homocysteine-added M9 media as described above. Accordingly, it was confirmed that homocysteine in an unknown sample does not affect the *Escherichia coli* Met5⁻-based quantitative analysis of methionine.

*Escherichia coli* MetB⁻ and *Escherichia coli* Met5⁻, of which use for homocysteine and methionine quantitative analysis was confirmed, were deposited under the Budapest treaty to Korean Culture Center of Microorganisms (KCCM) College of engineering Yonsei University, Hongje 1-dong Seodaemun-gu, 120-749 Seoul, Korea on Mar. 8, 2010, and their Accession numbers were KCCM11069P and KCCM11070P, respectively.

EXAMPLE 2

Quantitative Analysis of Homocysteine and Methionine 2-1. Preparation of Chip for Quantitative Analysis FIG. 1 schematically illustrates preparation of a chip for quantitative analysis of homocysteine and a method of determining the concentration of homocysteine in a sample by using the chip, according to embodiments of the present invention.

As described in Example 1-3, MetB⁻ and Met5⁻ auxotrophs were cultivated in LB media containing Cm and Km, respectively, at 37° C. with shaking for 9 to 12 hours. After the cells were washed with M9 media two times, $2\times10^6$ cells were mixed with 3% low melting agarose (Sigma-Aldrich, MO, USA) solution, which had been sterilized at high temperature and at high pressure, at a volume ratio of 1:1. 100 µl of the cell-agarose mixture was immobilized on each well of 96-well plate (Nunc, Rockilde, Denmark). After incubation at room temperature for 20 min, the cell-agarose mixture was solidified. Thereby, a quantitative analysis biochip including *Escherichia coli* MetB⁻ or *Escherichia coli* Met5⁻ immobilized on each well of a micro-plate was prepared.

2-2. Quantification of Methionine in Sample

As described in Example 2-1, a micro-well plate with *Escherichia coli* Met5⁻ immobilized thereon was prepared, and the content of methionine in a sample was measured by using the micro-well plate. To obtain a standard curve showing the relationship between luminescent intensity according to the *Escherichia coli* Met5⁻ growth and the concentration of methionine, a series of concentrations of methionine were added to a first row of the micro-well plate, and test samples, such as human plasma, were added to the remaining wells. 100 µl of M9 media containing 1 µl of 1 nM cyanocobalamin, 1 µl of 1 mM IPTG, a test sample or a methionine solution for obtaining a reference curve, were added to each well of the micro-well plate. After incubation at the temperature of 37° C. for 4 hours, 100 µl of a luciferin solution (1 mM D-luciferin in 0.1M sodium citrate (pH 5.0) buffer) was added thereto and incubated for 10 minutes. Then, luminescent intensities were measured using luminometer (Perkin Elmer, MA, USA), and scanned images thereof were obtained by using a cooled charge coupled device (CCD) camera (Fujifilm, Japan). Then, the concentration of methionine was calculated by using a standard curve showing a linearity between luminescent intensity according to the *Escherichia coli* Met5⁻ growth and the concentration of methionine.

Figure 5:
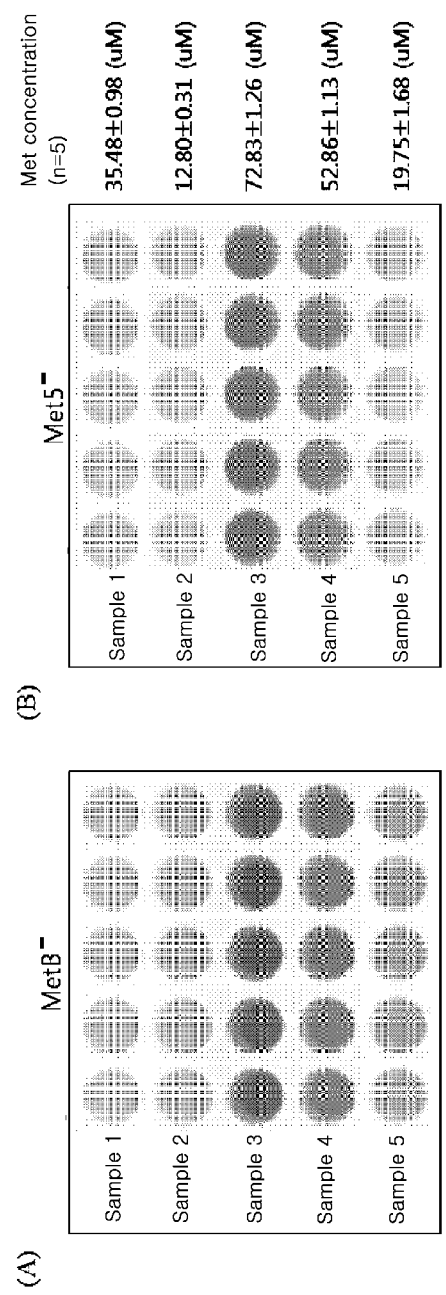
FIG. 5 illustrates methionine concentration measurements by *Escherichia coli* MetB⁻ and *Escherichia coli* Met5⁻ in 5 different plasma samples. (A) shows a scanned image of a luminescent signal generated from *Escherichia coli* MetB⁻ according to methionine concentrations, and (B) shows a scanned image of a luminescent signal generated from *Escherichia coli* Met5⁻ according to methionine concentrations. The respective samples were analyzed with five replicates, and the indicated values are mean±SD.

FIG. 5B shows methionine concentration measurements in samples, obtained from the luminescent intensity according to the growth of *Escherichia coli* Met5⁻.

2-3. Quantification of Homocysteine and Methionine in Sample

As illustrated in FIG. 1, to determine the concentration of homocysteine by using the two *Escherichia coli* mutants, a biochip with *Escherichia coli* Met5⁻ and *Escherichia coli* MetB⁻ immobilized thereon was prepared as described in Example 2-1. A series of concentrations of methionine were added to the first row in a region in which respective *Escherichia coli* Met5⁻ and *Escherichia coli* MetB⁻ were immobilized to obtain standard curves (1) and (2) showing the relationship between the luminescent intensity according to the *Escherichia coli* growth and the concentration of methionine. In addition, a series of concentrations of homocysteine were added to the second row in a region in which *Escherichia coli* MetB⁻ was immobilized to obtain a standard curve (3) showing the relationship between the luminescent intensity according to the *Escherichia coli* MetB⁻ growth and the concentration of homocysteine. Test samples, such as human plasma, were added to the remaining wells, and after incubation at a temperature of 37 for 4 hours, a substrate for luciferase was added thereto and a luminescent intensity thereof was measured. Thereafter, from the standard curve (1) showing the relationship between the methionine concentration and corresponding *Escherichia coli* Met5⁻ growth, the concentration of methionine in a test solution was determined. From the reference curve (2) showing the relationship between the methionine concentration and corresponding *Escherichia coli* MetB⁻ growth, a RLU value corresponding to an *Escherichia coli* MetB⁻ growth on methionine alone was calculated. Thereafter, the RLU value corresponding to an *Escherichia coli* MetB⁻ growth on methionine alone was subtracted from a total RLU value corresponding to *Escherichia coli* MetB⁻ growth in the test sample. Finally, a homocysteine concentration corresponding to the resulting RLU value was determined by referring to the standard curve (3) showing the relationship between RLU according to the *Escherichia coli* MetB⁻ growth and the concentration of homocysteine.

Accuracy of the quantitative analysis was evaluated by performing an analytical recovery test. A starting sample with 50 µM homocysteine dissolved in 20% amino acid cocktail solution was prepared. The sample was serially diluted by 2, 5, and 10 times. The diluted three samples were analyzed by this assay, and it was confirmed that homocysteine concentrations of test samples were similar to theoretical concentrations thereof. The precision of the assay was evaluated by CV (%), which means coefficient variation of five results measured from a sample, and Recovery (%), which is critical to the reproducibility. Assay results are shown in Table 1 below.

TABLE 1

Recovery test of serially diluted homocysteine concentrations dissolved in 20% amino acid cocktail solution

| Dilution | Theoretical Hcy (µM) | Observed Hcy[a] (µM) | SD[b] | CV[c] (%) | Recovery (%) |
|---|---|---|---|---|---|
| Undilute | 50 | 50.00 | — | — | 100.0 |
| 2 times | 25 | 24.94 | 0.62 | 2.5 | 100.2 |

TABLE 1-continued

Recovery test of serially diluted homocysteine concentrations dissolved in 20% amino acid cocktail solution

| Dilution | Theoretical Hcy (μM) | Observed Hcy[a] (μM) | SD[b] | CV[c] (%) | Recovery (%) |
|---|---|---|---|---|---|
| 5 times | 10 | 10.19 | 0.16 | 1.6 | 98.1 |
| 10 times | 5 | 4.92 | 0.15 | 3.1 | 101.7 |

[a]Mean of five measurements
[b]Standard deviation of five measurements
[c]Coefficient of variation In addition, a recovery test was conducted using five human plasma samples containing different concentrations of homocysteine. Results thereof are shown in Table 2. The concentrations of homocysteine in plasma sample were measured in advance by HPLC, and the results are indicated as original Hcy (μM) in Table 2. Five different concentrations (10, 20, 30, 40, and 50 μM) of homocysteine were added to the plasma samples, and final concentrations of homocysteine were measured by using the quantitative analysis method using *Escherichia coli* MetB[−] and *Escherichia coli* Met5[−]. FIG. 5A shows a scanned image illustrating luminescent signals of *Escherichia coli* MetB[−] grown in the test sample, and FIG. 5B shows that the methionine concentration in plasma samples are quantified by *Escherichia coli* Met5[−], along with five measurement results of the respective samples. As shown in Table 2 below, the homocysteine values measured in plasma samples were almost adjacent to the expected values, which were of the sums of the original Hcy and the added Hcy. The precision of this test was acceptable with the calculated CVs in a range of 3.4 to 5.7(%) and Recovery in a range of 96.3 to 104.1(%).

TABLE 2

Recovery test of human plasma samples with different concentrations of homocysteine (Hcy) added

| Sample No. | Original Hcy (μM) | Added Hcy (μM) | Expected Hcy (μM) | Measured Hcy[a] (μM) | SD[b] | CV[c] (%) | Recovery (%) |
|---|---|---|---|---|---|---|---|
| 1 | 9.35 | 10 | 19.35 | 20.03 | 0.86 | 4.3 | 96.6 |
| 2 | 10.26 | 20 | 30.26 | 31.17 | 1.06 | 3.4 | 97.1 |
| 3 | 11.75 | 30 | 41.75 | 43.34 | 1.79 | 4.1 | 96.3 |
| 4 | 12.76 | 40 | 52.76 | 50.68 | 2.16 | 4.3 | 104.1 |
| 5 | 13.94 | 50 | 63.94 | 63.34 | 3.62 | 5.7 | 100.9 |

Figure 6:
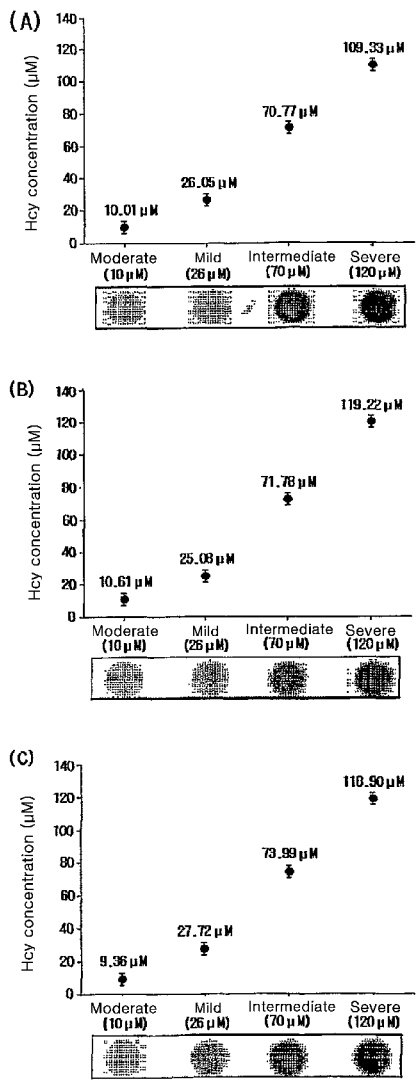
FIG. 6 shows results of homocysteine quantitative analysis for the diagnosis of hyperhomocysteinemia, performed using *Escherichia coli* MetB⁻ and *Escherichia coli* Met5⁻. (A) to (C) respectively show graphs of a luminescent intensity according to growth of *Escherichia coli* MetB⁻, with respect to a concentration of homocysteine dissolved in pure water, 20 µM methionine-containing water, and 20% amino acid cocktail solution, and luminescent intensities according to homocysteine concentrations. Tests were performed on samples with homocysteine concentrations (10, 26, 70, and 120 µM) representing the four stages of hyperhomocysteinemia (moderate, mild, Intermediate, and severe). The respective samples were analyzed with five replicates.

[a]Mean of five measurements
[b]Standard deviation of five measurements
[c]Coefficient of variation 2-4. Diagnosis of Hyperhomocysteinemia To verify quantitative ability of this assay, artificial samples containing four different homocysteine concentrations (10, 26, 70, and 120 μM) corresponding to four stages (moderate, mild, intermediate, and severe) of hyperhomocysteinemia were tested by the quantitative analysis described in Example 2-3. FIGS. 6A, 6B, and 6C respectively show quantitative analysis results of homocysteine samples dissolved in pure water, 20 μM methionine-containing water, and a 20% amino acid cocktail solution. These results show that the biochip with *Escherichia coli* MetB[−] and *Escherichia coli* Met5[−] immobilized thereon can be used to diagnose hyperhomocysteinemia and the stage thereof.

For test of clinical samples, blood samples of healthy volunteers were collected into tubes containing heparin. Plasma was separated from blood within 1 hour from the collection by centrifugation at 6,000 rpm at 4° C. for 30 min. The plasma was collected into sterile tubes and stored at −70° C. until use. To evaluate correlation between the homocysteine qualification method according to an embodiment of the present invention and the conventional HPLC method, conventional HPLC for homocysteine determination was performed at Daejeon Bio Venture Town according to the manufacturer's instructions and protocols. The accuracy and precision of the homocysteine qualification method according to an embodiment of the present invention were evaluated by Recovery [Recovery (%)=Measured value/Expected value×100] and CV (coefficient of variation) [CV (%)=SD/Average×100]. The within-assay variation was determined from the results of three parallel experimental set-ups, and the between-assay was performed with measurements of each sample over three days. The accuracy and precision of within-assay and between-assay were also evaluated by calculating Recovery (%) and CV (%).

To verify the accuracy and precision of within-assay and between-assay, four plasma samples containing different concentrations of homocysteine quantified by HPLC method were used for test. Assay results are shown in Table 3 below. The concentrations of four plasma samples were indicated as original Hcy (μM) in Table 3. 5, 10, 40, and 90 μM homocysteine was added to respective four plasma samples to prepare artificial hyperhomocysteinemia samples. As a result, the CVs for within-assay with three replicates in a single run and between-assay performed over three days were ≤2.9 and ≤7.1, respectively. Recovery rates of within-assay and between-assay were in a range of 99.1 to 103.5% and 97.5 to 105.5%, respectively. These precisions are within ranges reported for currently used assays (Boucher, J. L.; Charret, C.; Coudray-lucas, C.; Giboudeau, J.; Cynober, L. Clin. Chem. 1997, 43, 1421-1428; Refsum, H.; Smith, A. D.; Ueland, P. M.; Nexo, E.; Clarke, R.; McPartlin, J.; Johnston, C.; Engbaek, F.; Schneede, J.; McPartlin, C.; Scott, J. M. Clin. Chem. 2004, 50, 3-32; Dietzen, D. J.; Weindel, A. L.; Carayannopoulos, M. O.; Landt, M.; Normansell, E. T.; Reimschisel, T. E.; Smith, C. H. Rapid Commun. Mass Sp. 2008, 22, 3481-3488). Accordingly, this assay for the quantification of homocysteine and diagnosis of hyperhomocysteinemia from human plasma is deemed to be acceptably accurate, precise, and reproducible.

TABLE 3

(C) Within-assay and between-assay with four different plasma samples

| | Sample 1 | Sample 2 | Sample 3 | Sample 4 |
|---|---|---|---|---|
| Experimental condition | | | | |
| Original Hcy (μM) | 7.97 | 9.20 | 11.58 | 18.01 |
| Added Hcy (μM) | 5 | 10 | 40 | 90 |
| Expected Hcy (μM) | 12.97 | 19.20 | 51.58 | 108.01 |
| Hyperhomocysteinemia | moderate | mild | intermediate | severe |
| Assay Within-assay | | | | |
| Measured[a] (μM) | 12.81 | 19.37 | 50.28 | 104.32 |
| SD[b] | 0.37 | 0.26 | 0.47 | 1.20 |
| CV[c] (%) | 2.9 | 1.4 | 0.9 | 1.1 |
| Recovery (%) | 101.3 | 99.1 | 102.6 | 103.5 |
| Between-assay | | | | |
| Measured (μM) | 12.70 | 19.46 | 52.88 | 102.39 |
| SD | 0.90 | 0.46 | 1.80 | 1.49 |
| CV (%) | 7.1 | 2.4 | 3.4 | 1.5 |
| Recovery (%) | 102.2 | 98.6 | 97.5 | 105.5 |

[a]Mean of three measurements
[b]Standard deviation of three measurements
[c]Coefficient of variation Sequence List Free Text SEQ ID NO: 1 and SEQ ID NO: 2 cited in the present specification are shown on the attached sequence list.

The invention claimed is:

1. A method of quantifying homocysteine in a sample by using first and second methionine auxotrophic mutants of *Escherichia coli*, the method comprising:
   measuring the content of homocysteine and methionine in the sample by culturing a first methionine auxotrophic mutant of *Escherichia coli* in the sample, wherein the first methionine auxotrophic mutant of *Escherichia coli* is a homocysteine and methionine auxotrophic mutant,
   measuring the content of methionine in the sample by culturing a second methionine auxotrophic mutant of *Escherichia coli* in the sample, wherein the second methionine auxotrophic mutant of *Escherichia coli* is a methionine auxotrophic mutant, and
   determining the content of homocysteine by subtracting the content of methionine from the content of homocysteine and methionine in the sample, wherein the first and second methionine auxotrophic mutants of *Escherichia coli* each further comprise a gene encoding luciferase or a fluorescent protein, wherein the expression of the luciferase or the fluorescent protein is in proportion to the growth of the first and second methionine auxotrophic mutants of *Escherichia coli*, and wherein the content of homocysteine and methionine and the content of methionine are measured from the amount of expression of the luciferase or the fluorescent protein in the first and second methionine auxotrophic mutants of *Escherichia coli*, respectively.

2. The method of claim 1, wherein the first methionine auxotrophic mutant of *Escherichia coli* is *Escherichia coli* MetB⁻ deposited under the Accession No. KCCM11069P and the second methionine auxotrophic mutant of *Escherichia coli* is *Escherichia coli* Met5⁻ deposited under the Accession No. KCCM11070P.

3. The method of claim 2, wherein the culturing of *Escherichia coli* MetB⁻ or *Escherichia coli* Met5⁻ is conducted after mixing the sample with a transcription inducer that induces the luciferase expression in *Escherichia coli* MetB⁻ or *Escherichia coli* Met5⁻.

4. The method of claim 2, wherein the measuring of the content of homocysteine or methionine in the sample further comprises, after the culturing of the *Escherichia coli* MetB⁻ or *Escherichia coli* Met5⁻ in the sample, reacting the sample with a substrate for luciferase and measuring a luminescent intensity.

5. The method of claim 1, further comprising comparing the content of homocysteine determined in the sample with the content of homocysteine measured in a normal control subject.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Forward primer for MetB cassette

<400> SEQUENCE: 1
gtgtaggctg gagctgcttc gaagttccta                              30

<210> SEQ ID NO 2
<211> LENGTH: 32
<212> TYPE: DNA
<213> ORGANISM: Artificial Sequence
<220> FEATURE:
<223> OTHER INFORMATION: reverse primer for MetB cassette

<400> SEQUENCE: 2
catatgaata tcctccttag ttcctattcc ga                           32